United States Patent [19]

Yang

[11] Patent Number: 6,083,537
[45] Date of Patent: Jul. 4, 2000

[54] INTEGRATED METHOD FOR PROTECTING LOGS AND GREEN LUMBER FROM SAPSTAIN AND MOLD

[75] Inventor: Dian-Qing Yang, Sainte-Foy, Canada

[73] Assignee: Forintek Canada Corp., Vancouver, Canada

[21] Appl. No.: 09/084,799

[22] Filed: May 26, 1998

[51] Int. Cl.$^7$ .......................... A01N 59/00; A01N 25/00; A01N 63/04; A61L 2/00
[52] U.S. Cl. ...................... 424/715; 424/93.5; 424/413; 424/600; 424/715; 424/717; 428/541; 422/28
[58] Field of Search ........................... 422/28; 424/93.5, 424/715, 717, 195.1, 412, 413, 600; 428/540, 541

[56] References Cited

U.S. PATENT DOCUMENTS 4,780,341  10/1988  Chow ...................................... 427/440

FOREIGN PATENT DOCUMENTS

93/01923  2/1993  WIPO .

OTHER PUBLICATIONS

Farr et al., Fungi on plants and plant products in the United States (1989), The American Phytopathological Society, p. 715.

Alexander, M. 1997. Introduction to Soil Microbiology. 2nd ed., John Wiley and Sons, New York.

Bergman, O, T. Nilsson and P. Jerkeman. 1970. Reduction of microbial deterioration in outside chip storage by alkali treatment. Svensk Papperstidning 73:653–666.

Brock, T.D., D.W. Smith and M.T. Madigan. 1988. Biology of Microorganisms. 5th ed., Prentice–Hall, Englewood Cliffs, New Jersey.

Bruce, A. and J.L. Highley. 1991. Control of growth of wood decay basidiomycetes by *Trichoderma spp.* and other potentially antagonistic fungi. Forest Prod. J. 42:63–67.

Dawson–Andoh, B.E. and J. J. Morrell. 1992. Enhancing the performance of bioprotection agents by pretreatment with waterborne salts. Wood and Fiber Science 24:347–352.

Freitag, M., J.J. Morel and A. Bruce. 1991. Biological Protection of wood: status and prospects. Biodeterioration Abstr. 5:1–13.

Gilbert, P.G. 1988. Lumber quality protection chemical products used in B.C. sawmills and shipping terminals. Paper presented to the Whistler 88 Conference of the Air and Waste Management Association, Whistler, B.C. Nov.

Kaarik, A.A. Decomposition of wood. 1974. In Dixon, C.H. (ed.) Biology of Plant Litter Decomposition. pp. 129–174. Academic Press, London.

Land, C.J., Z.G. Banhidi and A. Albertsson. 1987. Cold–tolerant (psychrotrophic) moulds and blue stain fungi from softwood in Sweden, growth rates in relation to pH and temperature. Nord. J. Bot. 7:97–106.

McAfee, B. and M. Gignac. 1996. Two stage method for the protection of lumber against sapstain. U. S. Patent, Serial No. 5,534,252.

McAfee, B. and M. Gignac. 1997. Antisapstain protection of steam pasteurized hemlock and fir lumber treated with a biocide and the potential bioprotectant, *Gliocladium roseum*. Mat. and Org. 31:45–61.

Morrell, J. J. and C.M. Sexton. 1990. Evaluation of a biological agent for controlling basidiomycete attack of Douglas–fir and southern pine. Wood Fiber Sci. 22:10–21.

Morrell, J. J. and C.M. Sexton. 1992. Effect of nutrient regimes, temperature, pH, and wood sterilization method on performance of selected bioprotectants against wood staining fungi. International Research Group on Wood Preservation Document No IRG/WP/1551. Harrowgate, UK.

Morris, P. I., D.J. Dickinson and J. F. Levy. 1984. The nature and control of decay in creosoted electricity poles. Rec. 1984 Annu. Conv. Br. Wood Preserv. Assoc. p. 42–53.

Panasenko, V.T. 1967. Ecology of microfungi. The Botanical Review 33 (3) :189–215.

Seifert, K.A., C. Breuil, L. Rossignol, M. Best and J.N. Saddler. 1988. Screening for microorganisms with the potential for biological control of sapstain on unseasoned lumber. Mat and Org. 23:81–95.

Stranks, D.W. Scytalidin. 1976. hyalodendrin, cryptosporiopsin: aantibiotics for prevention of blue stain in white pine sapwood. Wood Science 9:110–112.

Zabel, B.A. and J.J. Morrell. 1992. Wood Microbiology—Decay and Its Prevention. Acedemic Press, New York.

*Primary Examiner*—John Pak
*Assistant Examiner*—Frank Choi
*Attorney, Agent, or Firm*—Barnes & Thornburg

[57] ABSTRACT

The present invention relates to a method for controlling sapstain and mold in wood using a biocontrol agent having a high pH tolerance and an alkaline solution. Biocontrol agents that do not discolor wood may be introduced onto wood or wood products to prevent sapstain and mold. The biocontrol agent grows on the wood surface and protects the wood against attack by stain or decay fungi. The application of an alkaline solution containing a biocontrol agent having a high pH tolerance to the wood product is very effective in controlling stain or decay fungi. The alkaline solution raises the pH of the wood to a level which impedes growth of other wood-inhabiting fungi but does not inhibit colonisation of the wood by the biocontrol agent.

7 Claims, 1 Drawing Sheet

INTEGRATED METHOD FOR PROTECTING LOGS AND GREEN LUMBER FROM SAPSTAIN AND MOLD

FIELD OF THE INVENTION

This invention relates to the field of microbiology and of biocontrol agents, and, more particularly, is concerned with a process of protecting logs and green lumber against sapstain and mold by the treatment of wood with a combination of an alkaline solution containing sodium carbonate and sodium bicarbonate and a biocontrol agent, such as *Gliocladium roseum* Bainier.

BACKGROUND OF THE INVENTION

Logs and lumber are subject to degradation from molds and sapstaining fungi during storage and shipment. Molds grow on the surface of wood and cause discoloration through the mass production of spores. Sapstaining fungi penetrate deeply into sapwood through their dark pigmented hyphae and stain wood to black, blueish or grey appearance. Customers for lumber place a high value on the appearance and quality of the product they receive. Wood stain can significantly reduce the value of the lumber by lowering its grade, resulting in monetary and market losses. To offset fungal discoloration, lumber is kiln dried or chemically treated after processing in sawmills. Although a growing amount of wood is kiln-dried, chemical treatment is still the main process for wood stain control for export lumber (Gilbert, 1988). Most of the chemicals in use are synthetic compounds and have a broad spectrum of activity. Public and government concern for the environment has put use of chemicals in sawmills under increasing scrutiny, and there remains an interest in exploring new products and technology for wood protection.

A better understanding of factors affecting growth of molds and staining fungi helps to develop rational chemical or biocontrol agents or develop physical protection methods against these fungi. In a practical sense, when the critical growth requisites of a wood-degrading fungus are known, it is sometimes feasible to modify wood handling or use practices which adversely affect fungus growth, thereby achieving prevention or economic control of the problem.

Like all living organisms, fungi need certain requirements for growth and survival. The major factors that affect the growth of wood-inhabiting fungi are substrate (food), water (above the fiber saturate point, greater than 20% water in wood), oxygen (more than 20% of the wood-void volume), a favorable temperature range, and a suitable pH value (Brock et al., 1988; Zabel & Morrell, 1992). Although many of these factors have been well studied, the effect of pH on the growth of wood staining fungi is not well documented.

Hydrogen ion concentration (pH) of the substrate is a main factor affecting substrate availability, exoenzyme stability, cell permeability and solubility of minerals and vitamins to microorganisms. It is widely acknowledged that fungi generally dominate in acidic environments (pH 3–6) although a wide range of pH (1.5–9.0) is often tolerated by wood inhabiting fungi (Kaarik, 1974; Alexander, 1977). Most wood decay basidiomycetes grow only at low pH values, and the brown rots (basidiomycetes) are particularly sensitive to high pH and often do not grow at pH above 6.5 (Kaarik, 1974). Molds and sapstaining fungi are more pH tolerant and may occur between pH 2 to 10 (Panasenko, 1967; Land et al., 1987). The growth of these wood-inhabiting fungi in wood can be reduced by alkali treatment (Bergman et al., 1970).

The use of biocontrol agents to protect wood from fungal degradation has been recognized as a possible alternative to chemical treatment and has received intensive investigation worldwide for many years (Freitag et al., 1991; Bruce & Highley, 1991; Stranks, 1976). In this strategy, fungi or bacteria that do not discolor wood are introduced onto lumber after cutting. These organisms grow on the wood surface and protect wood against attack by stain or decay fungi. This approach has worked well in laboratory testing for many microorganisms, but there has been limited field success (Morris et al., 1984; Morrell & Sexton, 1990).

*Gliocladium roseum* Bainier, also known as *Gliocladium aureum* Rader, has been identified as a potential biocontrol agent against sapstain on small blocks of softwood in laboratory tests (Seifert et al., 1988). This antagonist protected pasteurized lumber from stain (McAfee & Gignac, 1996), but showed inconsistent performance on green lumber in field testing (McAfee & Gignac, 1997). The poor performance of this fungus in lumber under natural conditions is due to the lack of a comprehensive competitive ability against other wood-inhabiting fungi. To improve the effectiveness of a biocontrol agent, one approach could be to selectively alter conditions of wood with a view to giving the promoting fungus a competitive advantage (Morrell & Sexton, 1992; Dawson-Andoh & Morrell, 1992).

SUMMARY OF THE INVENTION

It is an object of the present invention to improve the effectiveness of a biocontrol agent by selectively altering the pH value of wood with an alkaline solution to give the biocontrol agent a competitive advantage.

Thus according to a first broad aspect, the invention provides for an effective and environmentally compatible method of controlling sapstain and mold in wood and wood products using a combination of an alkaline solution and a biocontrol agent.

It is a particular feature of this invention to provide a method of controlling sapstain in wood comprising treating logs and green lumber with an aqueous alkaline solution which raises the pH of the wood product to a level which renders the growth of other wood inhabiting fungi unfavorable but does not inhibit colonisation of the logs and green lumber by the biocontrol agent.

In one embodiment, the wood is treated with a solution of sodium carbonate and sodium bicarbonate which increases the wood surface pH value. The higher wood surface pH impedes the growth of other wood inhabiting fungi and enhances colonisation of the biocontrol agent.

In a preferred embodiment, a solution containing about 4% Nt/vol of sodium carbonate, about 1% wt/vol of sodium bicarbonate and spores of *Gliocladium roseum* or *Gliocladium aureum* is applied to wood products.

The invention also provides a method of producing spores of the biocontrol agent *Gliocladium roseum* for use as an inoculum.

Within the context of the invention it is also contemplated to combine suitable alkalis with spores of a biocontrol agent having a high pH tolerance to make up a novel combination solution.

Furthermore, the invention relates to methods of using the combination solution to control sapstain and mold in logs and in lumber of unseasoned softwood.

BRIEF DESCRIPTION OF THE DRAWING

The accompanying drawing which is incorporated in and forms a part of the specification illustrates preferred embodiments of the present invention, and together with the description, serves to explain the principles of the invention. In the drawing.

DETAILED DESCRIPTION OF THE INVENTION

Figure 1:
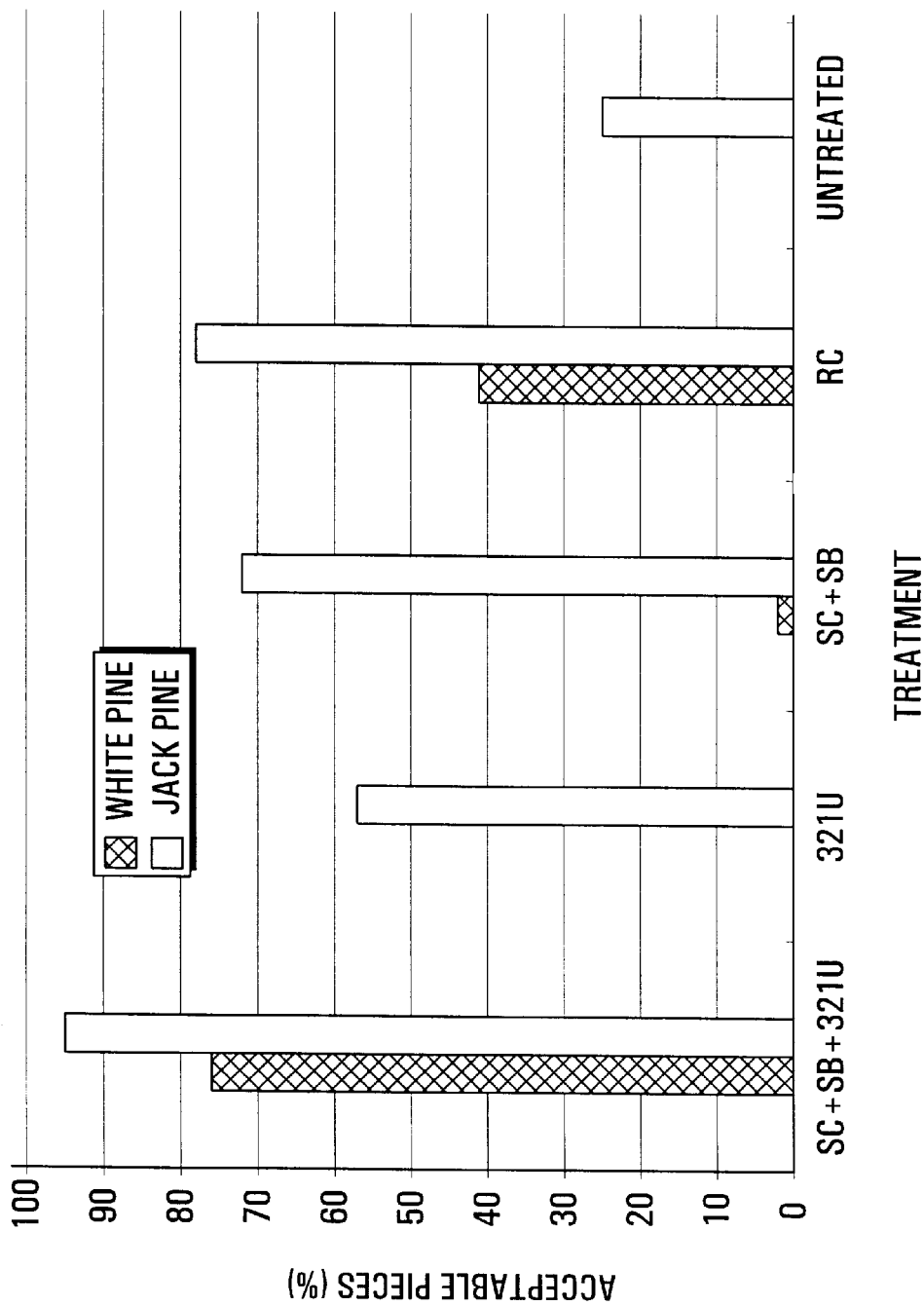
FIG. 1 is a graph illustrating growth of mold and sapstain in lumber of white pine and jack pine treated with different agents in a field test for 4 months.

Hydrogen ion concentration (pH) of the substrate is one of the main factors that affect fungal growth. The growth of fungi is favored at a pH range of about pH 3 to 6. Some wood decay basidiomycetes do not grow at a pH of above 6.5.

The alkaline solution of the invention has a pH value in the range of about pH 10.5–11.5 and, in any event, is sufficiently alkaline to raise the pH of the wood surface to within the range of pH 7–10.5, preferably within the range of pH 8.5 to 10. To obtain the appropriate pH level, an alkaline solution formed by the addition of sodium carbonate and sodium bicarbonate to an aqueous solution was used. Other suitable alkalis are sodium borate, sodium phosphate, sodium sulphate and the like.

The concentration of the alkaline solution applied to the wood allows for rapid colonisation of the biocontrol agent on the wood tissue. Rapid colonisation of the wood tissue is achieved by raising the surface pH of the wood to a level sufficient to favor growth of the biocontrol agent over growth of competing wood inhabiting fungi.

The invention combines the application to wood of both an alkaline solution and a biocontrol agent. The biological agent must be able to tolerate the surface pH value of the wood following application of the alkaline solution. A preferred biological agent is *Gliocladium roseum* or *Gliocladium aureum* but other biocontrol agents having a high pH tolerance could also be used.

*Gliocladium roseum* Bainier, also known as *Gliocladium aureum* (Forentek Culture Collection FCC 321U) isolated from root of carrot has been deposited with the Centraalbureau voor schimmelcultures, CBS 226.48 and the American Type Culture Collection, ATCC 10406. This fungus has demonstrated antagonistic activity to many other fungi. Because it is a colorless fungus and does not cause significant weight and strength losses of colonized wood, this microorganism has high potential to control sapstain in wood as well as tree diseases.

As previously indicated, *Gliocladium roseum* has been identified as a biological anti-sapstain agent. However, the performance of this microorganism has been reported to be poor on green lumber in field testing. The following examples describe in detail how the performance of this biocontrol agent is improved by the simultaneous application of a selected alkaline solution.

EXAMPLE 1

Wood wafers in size of 4 cm×2 cm×0.5 cm were cut from defect-free green sapwood of white pine and jack pine purchased from local sawmills. *G. roseum* was subcultured in Petri plates containing 2% malt extract agar (20 g malt extract and 20 g Difco agar in 1 L distilled water). The plates were incubated at 26° C. with continuous light for 14 days. Conidia formed were collected by adding 2 ml of sterile distilled water to each plate and gently agitating it with a glass rod. The final spore suspension was adjusted into $1\times10^6$ spores per ml of water. A mixed spore suspension ($1\times10^6$ spores/ml) was also prepared in the same way as with *G. roseum* using equal amounts of spores from the following ten sapstaining fungi: *Ophiostoma piceae* 387E, *Aureobasidium pullulans* 132S, *Ceratocystis adiposa* 251E, *Alternaria alternata* 2G, *Cladosporium sphaerospermum* 806B, *Hormonema dematioides* 742D, *Rhinocladiella atrovirens* 135E, *Ophiostoma minus* 864A, *Phialophora botulispora* 707C and *Ophiostoma piliferum* 55B.

Wood wafers were dipped for 30 seconds in the following solutions: 1) *G. roseum* spore suspension at $1\times10^6$ spores per ml of water; 2) an aqueous solution containing 4% sodium carbonate and 1% sodium bicarbonate; 3) an aqueous solution containing 4% sodium carbonate, 1% sodium bicarbonate and *G. roseum* spores at a concentration of $1\times10^6$ spores/ml; and 4) a reference anti-sapstain chemical containing didecyl dimethyl ammonium chloride (64%) and 3-iodo-2-propynyl butyl carbamate (7.6%) in a 1:80 dilution of the product in water. Untreated wafers served as control. After the treatment, each of the treated wafers, ten pieces per treatment, was immediately inoculated with 0.1 ml of the mixed sapstaining spore suspension and was placed, two pieces per plate, on a W-shaped glass supporter sitting on two layers of wet filter paper in a Petri plate. These plates were incubated in a growth chamber set at 26° C. and 75% Rh. Wood wafers were inspected for mold and sapstain growth after 8 and 16 weeks incubation based on a visual rating scale of 0 to 5 where: 0=no growth, 1=trace of growth, 2=little growth, 3=moderate growth, 4=heavy growth, and 5=very heavy growth. A wood wafer of lumber was rated as acceptable if it had a score of 2 or less.

Results showed that wood wafers treated with the solution containing 4% sodium carbonate, 1% sodium bicarbonate and spores of *G. roseum* gave a satisfactory level of protection with 100% acceptable pieces up to sixteen weeks, which was as good as for wood wafers treated with the reference chemical (Table 1). The treatment of both white pine and jack pine wood wafers with this mixture doubled the number of acceptable pieces as compared to the treatment with spores of *G. roseum* alone.

EXAMPLE 2

This example examined the efficacy of the different treatments on the protection of wood under a favorable environmental condition but without artificial inoculation of mold and sapstaining fungi. White pine and jack pine wood wafers and inoculum of *G. roseum* were prepared as in example 1. Wood wafers were treated in the same way as with the samples in example 1 but without the inoculation of sapstaining fungi after the treatment. Samples in this test, 30 wood wafers per treatment, were randomly placed in three replicate covered plastic bins, Three layers of paper towels were placed in the bottom of the bin and were wetted with 2 L of water. Plastic grids which supported the samples were put on the top of the paper, and the relative humidity inside the container was measured as 100%.

These bins were placed in a growth chamber set at 26° C. and 75% Rh, and wood wafers inside were inspected after 8 and 16 weeks. Mold and sapstain developed on each wafer was visually rated in the same way as that described in example 1. Data were subjected to analysis of variance (ANOVA) to compare the level of mold and sapstain amongst treatments. Following the ANOVA, the individual means were compared and ranked using Scheffe's test for multiple comparison.

In this test, wood wafers of white pine and jack pine treated with spores of *G. roseum* alone only provided partial protection from fungal sapstain during a sixteen-week testing period. However, adding 4% sodium carbonate and 1% sodium bicarbonate into the *G. roseum* spore suspension significantly increased the number of acceptable pieces of treated wood wafers (Table 2).

EXAMPLE 3

Field trials were performed on white pine and jack pine in Forintek Eastern Laboratory at Sainte-Foy, Quebec. *G. roseum* was subcultured on 2% malt extract agar at 26° C. for 7 days. Mycelium discs, 5 mm in diameter, were cut from the periphery of the colonies and transferred to 1-L flasks containing 500 ml of 1.5% malt extract broth (15 g malt extract broth in 1 L water). The culture was incubated for 7 days at 26° C. with agitation on a rotary shaker (100 rpm). Thereafter, spores and mycelia produced in the flasks were ground by a homogenizer at a low speed. The suspension was then centrifuged at 5,000 rpm for 15 minutes. The supernatant was poured off and the cell pellet was washed with sterile distilled water and collected by centrifugation.

Four aqueous solutions were prepared: a) *G. roseum* cell suspension adjusted to $1 \times 10^6$ propagules per ml of water, b) an aqueous solution containing 4% sodium carbonate and 1% sodium bicarbonate, c) *G. roseum* suspension ($1 \times 10^6$ propagules/ml) in 4% sodium carbonate and 1% sodium bicarbonate solution, and d) a reference anti-sapstain chemical in a 1:80 dilution of the product in water.

Freshly sawn, ungraded and clean lumber of white pine and jack pine was obtained from local sawmills and was cut into the size of 1"×4"×16". The boards were dipped in the different solutions separately one piece at a time. Each treatment contained 120 boards in three different packs (40 boards per pack), and untreated boards served as controls. The sets of boards treated with different solutions were piled side by side in the yard of Forintek. The pile was covered with a plastic sheet to prevent wood dry up and to create a favorable condition for the fungal growth. After four months storage, each board was rated for the development of mold, sapstain and decay individually based on the visual rating system describe in example 1. The board was considered as acceptable if the sum of scores of the three defects in this board was 2 or less.

The results of this test are shown in FIG. 1. On white pine wood, *G. roseum* alone or alkaline solution alone did not provide protection from sapstain while the combination of both agents significantly reduced the wood infection and increased the number of acceptable pieces. On jack pine wood, application of *G. roseum* alone only provided partial protection from fungal attack. However, adding 4% sodium carbonate and 1% sodium bicarbonate into the spore suspension significantly increased acceptable pieces of treated lumber. On both wood species, *G. roseum* in 4% sodium carbonate and 1% sodium bicarbonate solution gave better protection than the reference chemical did.

EXAMPLE 4

The evaluation of the combination of alkalis and the biocontrol agent against sapstain on logs was also conducted in field conditions. Black spruce logs were obtained from a local sawmill in the summer of 1997 and were cut into 80 cm in length. These logs were dipped in either a *G. roseum* cell suspension, or a suspension containing both *G. roseum* inoculum and the alkalis described in example 3. Logs treated with the reference chemical in a 1:40 dilution of the product in water as well as untreated logs served as controls. Each treatment contained 7 replicate logs, and all logs were closely piled in the Forintek backyard and covered with a plastic sheet to prevent dry up.

Extent of sapstain in logs was assessed after 4 months storage. Logs were cut into four 3 cm-thick discs from each end. Surface cover and maximal penetration of sapstain on the cross section was measured for each disc. A mean value was calculated from a total of 56 discs sawed from 7 replicate logs in each treatment. A statistical analysis was employed in the same way as in example 2, and the result is summarized in Table 3. Logs treated with the suspension containing both *G. roseum* and alkalis resulted in 2.2 times and 4.1 times less stained wood than that treated with *G. roseum* alone and untreated logs respectively. No significant difference existed between the treatments with the mixed solution and the reference chemical.

TABLE 1

Growth of mold and sapstain on wood wafers of white pine and jack pine treated with different agents in a laboratory test under conditions of inoculation with sapstaining fungi

| | Acceptable pieces (%) | | | |
| --- | --- | --- | --- | --- |
| | White pine | | Jack pine | |
| Treatment | 8 weeks | 16 weeks | 8 weeks | 16 weeks |
| $Na_2CO_3$ + $NaHCO_3$ + *G. roseum* | 100 | 100 | 100 | 100 |
| *G. roseum* | 80 | 50 | 90 | 80 |
| $Na_2CO_3$ + $NaHCO_3$ | 50 | 20 | 40 | 30 |
| Reference chemical (1:80) | 100 | 100 | 100 | 90 |
| Untreated | 10 | 0 | 50 | 10 |

TABLE 2

Growth of mold and sapstain on wood wafers of white pine and jack pine treated with different agents in a laboratory test under conditions of natural infection

| | Acceptable pieces (%) | | | |
| --- | --- | --- | --- | --- |
| | White pine | | Jack pine | |
| Treatment | 8 weeks | 16 weeks | 8 weeks | 16 weeks |
| $Na_2CO_3$ + $NaHCO_3$ + *G. roseum* | 100 | 100 | 100 | 100 |
| *G. roseum* | 70 | 40 | 97 | 87 |
| $Na_2CO_3$ + $NaHCO_3$ | 17 | 10 | 80 | 67 |
| Reference chemical (1:80) | 67 | 47 | 97 | 90 |
| Untreated | 7 | 3 | 63 | 47 |

TABLE 3

Development of mold and sapstain in logs of black spruce treated with different agents in a field test

| Treatment | % Stain coverage | Maximal penetration (mm) |
| --- | --- | --- |
| $Na_2CO_3$ + $NaHCO_3$ + *G. roseum* | 6.1 | 7.2 |
| *G. roseum* | 13.2 | 13.6 |
| Reference chemical (1:40) | 5.7 | 7.5 |
| Untreated | 25.0 | 13.9 |

REFERENCES

Alexander, M. 1977. Introduction to Soil Microbiology. 2nd ed., John Wiley and Sons, New York.

Bergman, O, T. Nilsson and P. Jerkeman. 1970. Reduction of microbial deterioration in outside chip storage by alkali treatment. Svensk Papperstidning 73:653–666.

Brock, T. D., D. W. Smith and M. T. Madigan. 1988. Biology of Microorganisms. 5th ed., PrenticeHall, Englewood Cliffs, N.J.

Bruce, A. and J. L. Highley. 1991. Control of growth of wood decay basidiomycetes by Trichoderma spp. and other potentially antagonistic fungi. Forest Prod. J. 42:63–67.

Dawson-Andoh, B. E. and J. J. Morrell. 1992. Enhancing the performance of bioprotection agents by pretreatment with waterborne salts. Wood and Fiber Science 24:347–352.

Freitag, M., J. J. Morel and A. Bruce. 1991. Biological protection of wood: status and prospects. Biodeterioration Abstr. 5:1–13.

Gilbert, P. G. 1988. Lumber quality protection chemical products used in B. C. sawmills and shipping terminals. Paper presented to the Whistler 88 Conference of the Air and Waste Management Association, Whistler, B. C. November.

Kaarik, A. A. Decomposition of wood. 1974. In Dixon. C. H. (ed.) Biology of Plant Litter Decomposition. pp. 129–174. Academic Press, London.

Land, C. J., Z. G. Banhidi and A. Albertsson. 1987. Cold-tolerant (psychrotrophic) moulds and blue stain fungi from softwood in Sweden, growth rates in relation to pH and temperature. Nord. J. Bot. 20 7:97–106.

McAfee, B. and M. Gignac. 1996. Two stage method for the protection of lumber against sapstain. U.S. Pat. No. 5,534,252.

McAfee, B. and M. Gignac. 1997. Antisapstain protection of steam pasteurized hemlock and fir lumber treated with a biocide and the potential bioprotectant, *Gliocladium roseum*. Mat. and Org. 31:45–61.

Morrell, J. J. and C. M. Sexton. 1990. Evaluation of a biological agent for controlling basidiomycete attack of Douglas-fir and southern pine. Wood Fiber Sci. 22:10–21.

Morrell, J. J. and C. M. Sexton. 1992. Effect of nutrient regimes, temperature, pH, and wood sterilization method on performance of selected bioprotectants against wood staining fungi. International Research Group on Wood Preservation Document No IRG/WP/1551. Harrowgate, UK.

Morris, P. I., D. J. Dickinson and J. F. Levy. 1984. The nature and control of decay in creosoted electricity poles. Rec. 1984 Annu. Conv. Br. Wood Preserv. Assoc. p. 42–53.

Panasenko, V. T. 1967. Ecology of microfungi. The Botanical Review 33(3):189–215.

Seifert, K. A., C. Breuil, L. Rossignol, M. Best and J. N. Saddler. 1988. Screening for microorganisms with the potential for biological control of sapstain on unseasoned lumber. Mat and Org. 23:81–95.

Stranks, D. W. Scytalidin. 1976. hyalodendrin, cryptosporiopsin: antibiotics for prevention of blue stain in white pine sapwood. Wood Science 9:110–112.

Zabel, B. A. and J. J. Morrell. 1992. Wood Microbiology—Decay and Its Prevention. Academic Press, New York.

We claim:

1. A method of controlling sapstain in wood or a wood product comprising treating the wood or wood product with an alkaline solution containing at least one biocontrol organism having a high pH tolerance comprising an effective amount of an inoculum of *Gliocladium roseum* to colonize the wood or wood product, wherein application of the solution raises the pH of the surface of the wood or wood product to within a range of pH 7 to 10.5, wherein the solution is rendered alkaline by the addition of at least one inorganic alkaline compound.

2. A method according to claim 1 wherein the solution is rendered alkaline by sodium carbonate and sodium bicarbonate.

3. A method according to claim 1 wherein the wood products comprise softwood.

4. The method according to claim 5 wherein said softwood is white pine, jack pine or black spruce.

5. The method according to claim 1 wherein the wood or wood products comprise lumber, logs or wood chips.

6. A method according to claim 1 wherein said at least one inorganic alkaline compound comprises about 4% wt/vol sodium carbonate and about 1% wt/vol sodium bicarbonate.

7. A wood or wood product treated according to the method of claim 1.

* * * * *

UNITED STATES PATENT AND TRADEMARK OFFICE
CERTIFICATE OF CORRECTION

PATENT NO. : 6,083,537
DATED : July 4, 2000
INVENTOR(S) : Dian-Qing Yang

It is certified that error appears in the above-identified patent and that said Letters Patent is hereby corrected as shown below:

Column 8,
Line 23: change "pH 7 to 10.5" to "pH 7 to 10.5"
Line 31: change "method according to claim 5" to method according to claim 3"

Signed and Sealed this

Seventh Day of August, 2001

Attest:

NICHOLAS P. GODICI
Attesting Officer     Acting Director of the United States Patent and Trademark Office